United States Patent [19]
Jackson et al.

[11] Patent Number: 5,880,112
[45] Date of Patent: Mar. 9, 1999

[54] NAALADASE INHIBITORS

[75] Inventors: Paul F. Jackson, Bel Air; Barbara S. Slusher, Kingsville, both of Md.

[73] Assignee: Guilford Pharmaceuticals Inc., Baltimore, Md.

[21] Appl. No.: 833,646

[22] Filed: Apr. 8, 1997

Related U.S. Application Data

[62] Division of Ser. No. 665,776, Jun. 17, 1996, Pat. No. 5,672,592.

[51] Int. Cl.$^6$ .................................................. A61K 31/66
[52] U.S. Cl. ........................... 514/121; 514/114; 514/75
[58] Field of Search ........................... 514/75, 114, 121

[56] References Cited

U.S. PATENT DOCUMENTS

| | | | |
|---|---|---|---|
| 3,472,932 | 10/1969 | Shindo et al. | 424/210 |
| 4,151,172 | 4/1979 | Ondetti et al. | 260/326.2 |
| 4,168,267 | 9/1979 | Petrillo, Jr. | 260/326.2 |
| 4,316,896 | 2/1982 | Thorsett et al. | 548/341 |
| 4,337,201 | 6/1982 | Petrillo, Jr. | 548/413 |
| 4,374,131 | 2/1983 | Petrillo, Jr. | 546/22 |
| 4,444,765 | 4/1984 | Karanewsky et al. | 546/22 |
| 4,448,772 | 5/1984 | Karanewsky | 546/22 |
| 4,452,790 | 6/1984 | Karanewsky et al. | 546/22 |
| 4,452,791 | 6/1984 | Ryono et al. | 546/22 |
| 4,468,519 | 8/1984 | Krapcho | 548/409 |
| 4,547,324 | 10/1985 | Wong et al. | 260/502.4 R |
| 4,555,506 | 11/1985 | Karanewsky et al. | 514/91 |
| 4,560,680 | 12/1985 | Ryono et al. | 514/82 |
| 4,560,681 | 12/1985 | Karanewsky | 514/82 |
| 4,567,166 | 1/1986 | Karanewsky et al. | 514/82 |
| 4,616,005 | 10/1986 | Karanewsky et al. | 514/80 |
| 4,703,043 | 10/1987 | Karanewsky et al. | 514/80 |
| 4,715,994 | 12/1987 | Parsons et al. | 260/502.5 E |
| 4,716,155 | 12/1987 | Karanewsky et al. | 514/89 |
| 4,849,525 | 7/1989 | Weller, III et al. | 548/413 |
| 4,885,283 | 12/1989 | Broadhurst et al. | 514/78 |
| 4,906,779 | 3/1990 | Weber et al. | 564/238 |
| 4,962,097 | 10/1990 | Parsons et al. | 514/114 |
| 4,988,681 | 1/1991 | Ishikawa et al. | 514/53 |
| 4,994,446 | 2/1991 | Sokolovsky et al. | 514/75 |
| 5,030,732 | 7/1991 | Morita et al. | 548/344 |
| 5,041,644 | 8/1991 | Morita et al. | 562/565 |
| 5,061,806 | 10/1991 | Morita et al. | 548/112 |
| 5,093,525 | 3/1992 | Weber et al. | 564/238 |
| 5,099,063 | 3/1992 | Parsons et al. | 562/16 |
| 5,143,908 | 9/1992 | Parsons et al. | 514/114 |
| 5,145,990 | 9/1992 | Parsons et al. | 514/79 |
| 5,147,867 | 9/1992 | Parsons et al. | 514/114 |
| 5,190,976 | 3/1993 | Weber et al. | 514/634 |
| 5,242,915 | 9/1993 | Ueda et al. | 514/210 |
| 5,262,568 | 11/1993 | Weber et al. | 564/238 |
| 5,336,689 | 8/1994 | Weber et al. | 514/634 |
| 5,508,273 | 4/1996 | Beers et al. | 514/141 |
| 5,538,957 | 7/1996 | Tsaklakidis et al. | 514/114 |
| 5,698,402 | 12/1997 | Luderer et al. | 435/74 |

OTHER PUBLICATIONS

Pudovik, A.N. et al., "Reaction of Partial Esters of Phosphorus Acids with Ethyl Benzoylformate," *Chemical Abstracts*, (1969) Abstract No. 69:87, 915u, *Zh. Obshch, Khim.* (1969) 1968, 38 (7), 1539–45 (Russ.).

Pudovik, A.N. et al., "Reactions of Ethyl Hydrogen Phenylphosphonite with Esters of α–Oxocarboxylic and α–Oxophosphonic Acids," *Chemical Abstracts*, (1969) Abstract No. 71:61,476x, *Zh. Obshch, Khim.* (1969) 39(5), 1021–7 (Russ.).

Shindo, N. et al., "O–alkyl (S–alkoxycarbonyl) (phenyl) methyl phenylthiophosphonate," *Chemical Abstracts*, (1970) Abstract No. 73:25,664q, 1970, Japan 70–03772.

Campbell, D.A., "The Synthesis of Phosphonate Esters, an Extension of the Mitsunobu Reaction," *Journal of Organic Chemistry*, (1992) 57:6331–6335.

*Primary Examiner*—Jerome D. Goldberg
*Attorney, Agent, or Firm*—Gary M. Nath; Todd L. Juneau; Nath & Associates

[57] ABSTRACT

The present disclosure relates to dipeptidase inhibitors, and more particularly, to N-Acetylated α-Linked Acidic Dipeptidase (NAALADase) enzyme inhibitors which are proposed as novel agents for the treatment of prostate cancer. NAALADase is enzyme which is a membrane-bound metalloprotease which hydrolyzes the dipeptide, N-acetyl-L-aspartate-L-glutamate (NAAG) to yield glutamate and N-acetylaspartate. The compounds of the present invention include phosphinic acid derivatives that inhibit NAALADase enzyme activity and which have been found useful for inhibiting the growth of prostate cancer cells.

9 Claims, 2 Drawing Sheets

NAALADASE INHIBITORS

This application is a Divisional of U.S. patent application Ser. No. 08/665,776, filed Jun. 17, 1996, now U.S. Pat. No. 5,672,592.

BACKGROUND OF THE INVENTION

1. Field of the Invention

The present invention relates to novel compounds and compositions which inhibit N-Acetylated α-Linked Acidic Dipeptidase (NAALADase) enzyme activity, and in particular to phosphinic acid compounds or phosphinic acid compositions which inhibit NAALADase enzyme activity in humans and warm-blooded animals. The present invention is also directed to novel compounds and compositions which inhibit N-Acetylated α-Linked Acidic Dipeptidase (NAALADase) enzyme activity as novel agents for treatment of cancer. Further, the present invention is directed to novel compounds and compositions which inhibit N-Acetylated α-Linked Acidic Dipeptidase (NAALADase) enzyme activity as novel agents for treatment of diseases of the prostate.

2. Description of the Prior Art

Prostate Cancer

Prostate cancer is now the leading form of cancer among men and the second most frequent cause of death from cancer in men. It is estimated that more than 165,000 new cases of prostate cancer were diagnosed in 1993, and more than 35,000 men died from prostate cancer in that year. Additionally, the incidence of prostate cancer has increased by 50% since 1981, and mortality from this disease has continued to increase. Previously, most men died of other illnesses or diseases before dying from their prostate cancer. We now face increasing morbidity from prostate cancer as men live longer and the disease has the opportunity to progress.

Current therapies for prostate cancer focus exclusively upon reducing levels of dihydrotestosterone to decrease or prevent growth of prostate cancer.

In addition to the use of digital rectal examination and transrectal ultrasonography, prostate-specific antigen (PSA) concentration is frequently used in the diagnosis of prostate cancer.

Prostate Specific Antigen

One well known prostate cancer marker is Prostate Specific Antigen (PSA). PSA is a protein produced by prostate cells and is frequently present at elevated levels in the blood of men who have prostate cancer. PSA has been shown to correlate with tumor burden, serve as an indicator of metastatic involvement, and provide a parameter for following the response to surgery, irradiation, and androgen replacement therapy in prostate cancer patients. It should be noted that Prostate Specific Antigen (PSA) is a completely different protein from Prostate Specific Membrane Antigen (PSMA). The two proteins have different structures and functions and should not be confused because of their similar nomenclature.

Prostate Specific Membrane Antigen (PSMA)

In 1993, the molecular cloning of a prostate-specific membrane antigen (PSMA) was reported as a potential prostate carcinoma marker and hypothesized to serve as a target for imaging and cytotoxic treatment modalities for prostate cancer. Antibodies against PSMA have been described and examined clinically for diagnosis and treatment of prostate cancer. In particular, Indium-111 labelled PSMA antibodies have been described and examined for diagnosis of prostate cancer and itrium-labelled PSMA antibodies have been described and examined for the treatment of prostate cancer.

PSMA is expressed in prostatic ductal epithelium and is present in seminal plasma, prostatic fluid and urine In 1996, it was found that the expression of PSMA cDNA actually confers the activity of NAALADase. This is entirely unexpected because until recently NAALADase research has been limited to its role in the brain and its effect on neurotransmitters whereas PSMA has been described and examined for the diagnosis and therapy of prostate cancer.

NAAG and NAALADase within the Central Nervous System

In a totally separate research area, efforts to examine the role of glutamate toxicity in diseases of the brain, i.e. epilepsy, amyotrophic lateral sclerosis (ALS), schizophrenia, and Alzheimer's disease, led researchers in an attempt to ascertain the exact role of NAALADase and NAAG in the central nervous system (CNS).

The dipeptide N-acetyl-L-aspartate-L-glutamate (NAAG) is a major peptidic component of the brain, with levels comparable to that of the major inhibitory neurotransmitter γ-aminobutyric acid (GABA). Although NAAG was first isolated in 1964, there was little activity toward elucidating its role in the central nervous system (CNS) until the deleterious nature of excess glutamate in a variety of disease states became apparent. Due to its structural similarity to glutamate, NAAG has been suggested to have a variety of roles similar to those of glutamate itself, including functioning as a neurotransmitter or a cotransmitter in the CNS. N-acetyl-aspartyl-glutamate (NAAG) is an abundant nervous system specific peptide which is present in synaptic vesicles and released upon neuronal stimulation in several systems. Several investigators have hypothesized that NAAG is involved in neuronal communication as a neurotransmitter, neuromodulator, or as a precursor of the neurotransmitter glutamate. In 1985, NAAG was reported to cause excitation of neurons of the lateral olfactory tract; however, it was subsequently demonstrated that these findings were due to an artifact of the preparation. More recently, NAAG was shown to elicit excitatory responses both in vitro and in vivo. However, under both scenarios, NAAG was less potent than glutamate. In 1988, a brain enzyme was identified which hydrolyzes NAAG to N-acetylaspartate (NAA) and glutamate (See FIG. 1).

NAALADase FIG. 1—Catabolism of NAAG by the peptidase NAALADase.

NAAG

NAA          GLU

Since NAALADase has been primarily researched for its role in the neurological field, much of what is known about NAALADase comes from neurological studies. N-acetylated α-linked acidic dipeptidase (NAALADase) is a membrane-bound metallopeptidase which catabolizes NAAG to N-acetylaspartate (NAA) and glutamate. Since it is possible that NAAG may not be the sole substrate for this enzyme in vivo, this peptidase was named N-acetylated α-linked acidic dipeptidase (NAALADase) for its structural specificity for N-acetylated acidic dipeptides. It has been demonstrated that [$^3$H]NAAG is degraded in vivo by an enzyme with the pharmacological characteristics of NAALADase. These data support a role for NAALADase in the metabolism of endogenous NAAG. Research has identified NAALADase as having a denatured molecular mass of 94 kDa.

Rat NAALADase activity has been extensively characterized and demonstrates a high affinity for hydrolysis of its putative substrate NAAG, with a Km=140 nM. Recently, NAALADase also has been shown to cleave the non-acetylated peptide, aspartylglutamate, with high affinity. Research has also found that the enzyme is membrane-bound, stimulated by chloride ions, and inhibited by polyvalent cation chelators, suggesting that it is a metallopeptidase.

In mammals, NAALADase is enriched in synaptic plasma membranes and is primarily localized to neural tissue and kidney. NAALADase has not been found in large quantities in the mammalian liver, heart, pancreas, or spleen. Prior to the present invention, NAALADase has not been found in prostate tissue.

Toward this end, NAAG and NAALADase have been examined in several different human and animal pathological conditions. It has been demonstrated that intra-hippocampal injections of NAAG elicit prolonged seizure activity. More recently, it was reported that rats genetically prone to epileptic seizures have a persistent increase in their basal level of NAALADase activity. These observations are consistent with the hypothesis that increased availability of synaptic glutamate elevates seizure susceptibility, and suggest that NAALADase inhibitors may provide anti-epileptic activity.

NAAG and NAALADase have also been implicated in the pathogenesis of ALS and in the pathologically similar animal disease called Hereditary Canine Spinal Muscular Atrophy (HCSMA). It has been shown that concentrations of NAAG and its metabolites-NAA, glutamate and aspartate-are elevated two- to three-fold in the cerebrospinal fluid of ALS patients and HCSMA dogs In addition, NAALADase activity is significantly increased (two- to three-fold) in post-mortem spinal cord tissue from ALS patients and HCSMA dogs. Although highly speculative, NAALADase inhibitors may be clinically useful in curbing the progression of ALS if increased metabolism of NAAG is responsible for the alterations of CSF levels of these acidic amino acids and peptides. Abnormalities in NAAG levels and NAALADase activity have also been documented in post-mortem schizophrenic brain, specifically in the prefrontal and limbic brain regions, underscoring the importance of examining the metabolism of NAAG in the pathophysiology of schizophrenia.

The identification and purification of NAALADase led to the proposal of another role for NAAG: specifically that the dipeptide may serve as a storage form of synaptic glutamate.

NAALADase Inhibitors

Only a few NAALADase inhibitors have been identified and those that have been identified have only been used in non-clinical neurological research. Examples of such inhibitors include general metallopeptidase inhibitors such as o-phenanthrolene, metal chelators such as EGTA and EDTA, and peptide analogs such as quisqualic acid and beta-NAAG.

SUMMARY OF THE INVENTION

The present invention is based upon the surprising discovery that NAALADase inhibitors exhibit a significant inhibitory effect on the growth of cancer cells, and particularly prostate cancer cells. The present disclosure relates to novel compositions containing dipeptidase inhibitors, and more particularly, to compounds and compositions which inhibit N-Acetylated α-Linked Acidic Dipeptidase (NAALADase) enzyme activity useful for treatment for diseases of the prostate, particularly, prostate cancer. Furthermore, as has been found in other tissues of the body, NAALADase inhibitors may show efficacy in the treatment of other forms of cancer. NAALADase is an enzyme which is a membrane-bound metalloprotease that hydrolyzes the dipeptide, N-acetyl-L-aspartate-L-glutamate (NAAG) to yield glutamate and N-acetylaspartate. The compounds and compositions of the present invention include phosphinic acid derivatives that inhibit NAALADase enzyme activity and which have been found useful for inhibiting the growth of prostate cancer cells.

Preferred compositions of the present invention include compounds having the following formula:

where
R is a $C_1$–$C_9$ straight or branched chain alkyl or alkenyl group, $C_3$–$C_8$ cycloalkyl, $C_3$ or $C_5$ cycloalkyl, $C_5$–$C_7$ cycloalkenyl, or $Ar_1$.

The present invention also contemplates the use of said alkyl, alkenyl, cycloalkyl, cycloalkenyl or aryl groups to be optionally substituted with $C_3$–$C_8$ cycloalkyl, $C_3$ or $C_5$ cycloalkyl, $C_5$–$C_7$ cycloalkenyl, $C_1$–$C_4$ alkyl, $C_1$–$C_4$ alkenyl, hydroxy, halo, hydroxyl, nitro, trifluoromethyl, $C_1$–$C_6$ straight or branched chain alkyl or alkenyl, $C_1$–$C_4$ alkoxy, $C_1$–$C_4$ alkenyloxy, phenoxy, benzyloxy, amino, or $Ar_1$, and where $Ar_1$ is selected from the group consisting of 1-napthyl, 2-napthyl, 2-indolyl, 3-indolyl, 2-furyl, 3-furyl, 2-thienyl, 3-thienyl, 2-, 3-, or 4-pyridyl, or phenyl, having one to three substituents which are independently selected from the group consisting of hydrogen, halo, hydroxyl, nitro, trifluoromethyl, $C_1$–$C_6$ straight or branched alkyl or alkenyl, $C_1$–$C_4$ alkoxy or $C_1$–$C_4$ alkenyloxy, phenoxy, benzyloxy, and amino; or pharmaceutically acceptable salts or hydrates thereof.

Especially preferred compounds of the present invention are selected from the group consisting of:
2-[[methylhydroxyphosphinyl]methyl]pentanedioic acid;
2-[[ethylhydroxyphosphinyl]methyl]pentanedioic acid;
2-[[propylhydroxyphosphinyl]methyl]pentanedioic acid;
2-[[butylhydroxyphosphinyl]methyl]pentanedioic acid;
2-[[cyclohexylhydroxyphosphinyl]methyl]pentanedioic acid;
2-[[phenylhydroxyphosphinyl]methyl]pentanedioic acid;
2-[[2-(tetrahydrofuranyl)hydroxyphosphinyl]methyl] pentanedioic acid;
2-[[(2-tetrahydropyranyl)hydroxyphosphinyl]methyl] pentanedioic acid;
2-[[((4-pyridyl)methyl)hydroxyphosphinyl]methyl] pentanedioic acid;
2-[[((2-pyridyl)methyl)hydroxyphosphinyl]methyl] pentanedioic acid;
2-[[(phenylmethyl)hydroxyphosphinyl]methyl]pentanedioic acid;
2-[[((2-phenylethyl)methyl)hydroxyphosphinyl]methyl] pentanedioic acid;
2-[[((3-phenylpropyl)methyl)hydroxyphosphinyl]methyl] pentanedioic acid;
2-[[((3-phenylbutyl)methyl)hydroxyphosphinyl]methyl] pentanedioic acid;
2-[[((2-phenylbutyl)methyl)hydroxyphosphinyl]methyl] pentanedioic acid;
2-[[(4-phenylbutyl)hydroxyphosphinyl]methyl] pentanedioic acid; and
2-[[(aminomethyl)hydroxyphosphinyl]methyl]pentanedioic acid.

Compounds of the present invention which are highly preferred are selected from the group consisting of:
2-[[methylhydroxyphosphinyl]methyl]pentanedioic acid;
2-[[ethylhydroxyphosphinyl]methyl]pentanedioic acid;
2-[[propylhydroxyphosphinyl]methyl]pentanedioic acid; and
2-[[phenylhydroxyphosphinyl]methyl]pentanedioic acid.

Compositions within the scope of the present invention contain the above described compounds and are formulated with a suitable pharmaceutical carrier. Such carriers are formulated in order to best utilize the compound for a particular purpose. Exemplary purposes include but are not limited to inhibition of tumor growth, inhibition of tumor cell growth, and inhibition of NAALADase enzyme activity. A particularly preferred tumor type or tumor cell type is prostatic adenocarcinoma.

Yet another preferred embodiment is directed to a composition for treating prostate diseases selected from the group consisting of prostate cancer and benign prostatic hyperplasia in an animal, which comprises: (i) the compound described above and (ii) a pharmaceutically acceptable carrier for administering said compound to said animal.

Further preferred embodiments include the use of additional therapeutic agents useful for treating diseases of the prostate. Such agents may be selected from the group consisting of: therapeutic hormones, chemotherapeutic agents, monoclonal antibodies, anti-angiogenesis agents, and radiolabelled compounds. The agent can also include any pharmaceutical compound useful for the treatments described herein to be delivered in combination with the compounds and compositions of the present invention.

BRIEF DESCRIPTION OF THE FIGURES

FIG. 1 shows the effect of 7-day treatment with quisqualate on the growth of LNCAP cells. Concentrations ranging from 10 nM to 1 μM of quisqualate show a sharp dose-dependent decrease of LNCAP cell proliferation as indicated by the significant decrease in the incorporation of [3H]thymidine.

FIG. 2 shows the effect of 7-day treatment with 2-(phosphonomethyl) pentanedioic acid on the growth of LNCAP cells. Concentrations ranging from 100 pM to 10 nM of 2-(phosphonomethyl)pentanedioic acid show a sharp dose-dependent decrease of LNCAP cell proliferation as indicated by the significant decrease in the incorporation of [3H] thymidine.

DETAILED DESCRIPTION OF THE INVENTION

The present invention pertains to compositions containing dipeptidase inhibitors, and more particularly, to those containing N-Acetylated α-Linked Acidic Dipeptidase (NAALADase) enzyme inhibitors which are useful as novel agents for the treatment of prostate cancer. Because NAALADase enzyme has been found in other tissues in the body, the compounds of the present invention are also useful for the treatment of other forms of cancer. For example, the kidney, brain, and testis have NAALADase present. As a result, in these examples, the compounds would be useful for treatments for brain cancer, kidney cancer, or testicular cancer. Other tissues will correlate with other treatments accordingly.

NAALADase is an enzyme which is a membrane-bound metalloprotease that hydrolyzes the dipeptide, N-acetyl-L-aspartate-L-glutamate (NAAG) to yield glutamate and N-acetylaspartate. The compounds of the present invention include phosphinic acid derivatives that inhibit NAALADase enzyme activity and which have been found useful for inhibiting the growth of prostate cancer cells.

Preferred compositions of the present invention include compounds having the following formula:

where
R is a $C_{-C9}$ straight or branched chain alkyl or alkenyl group, $C_3$–$C_8$ cycloalkyl, $C_3$ or $C_5$ cycloalkyl, $C_5$–$C_7$ cycloalkenyl, or $Ar_1$.

The present invention also contemplates the use of said alkyl, alkenyl, cycloalkyl, cycloalkenyl or aryl groups to be optionally substituted with $C_3$–$C_8$ cycloalkyl, $C_3$ or $C_5$ cycloalkyl, $C_5$–$C_7$ cycloalkenyl, $C_1$–$C_4$ alkyl, $C_1$–$C_4$ alkenyl, hydroxy, halo, hydroxyl, nitro, trifluoromethyl, $C_1$–$C_6$ straight or branched chain alkyl or alkenyl, $C_1$–$C_4$ alkoxy, $C_1$–$C_4$ alkenyloxy, phenoxy, benzyloxy, amino, or $Ar_1$, and where $Ar_1$, is selected from the group consisting of 1-napthyl, 2-napthyl, 2-indolyl, 3-indolyl, 2-furyl, 3-furyl, 2-thienyl, 3-thienyl, 2-, 3-, or 4-pyridyl, or phenyl, having one to three substituents which are independently selected from the group consisting of hydrogen, halo, hydroxyl, nitro, trifluoromethyl, $C_1$–$C_6$ straight or branched alkyl or alkenyl, $C_1$–$C_4$ alkoxy or $C_1$–$C_4$ alkenyloxy, phenoxy, benzyloxy, and amino; or pharmaceutically acceptable salts or hydrates thereof.

Other embodiments of the present invention are directed to pharmaceutical compositions for treating cancer, preventing growth of a cancer, for inhibiting the growth or differentiation of a cancer, for treating prostate diseases such as prostate cancer and benign prostatic hyperplasia, and for inhibiting NAALADase activity in an organism. It should be noted that such compositions can be utilized in methods of treatment, prevention, inhibition, and so forth, by persons of ordinary skill in the art.

Further preferred embodiments include the use of additional therapeutic agents. Such agents may be selected from the group consisting of: therapeutic hormones, chemotherapeutic agents, monoclonal antibodies, anti-angiogenesis agents, and radiolabelled compounds. Radiolabelled compounds and monoclonal antibodies may be used in a manner so as to provide diagnostic information. Examples of diagnostic information and uses include determining the type of disease, the progress of the particular disease, the location of cells targeted by a NAALADase inhibitor, radiolabelled compound or monoclonal antibody, and similar diagnostic uses known to persons skilled in the art.

It has been unexpectedly found that the right hand side of the phosphinic acid structure depicted above is necessary for substrate recognition by NAALADase enzyme. Thus, the present invention only contemplates substitutions to the left hand side of the phosphinic acid structure above, as indicated in the R group.

"NAALADase" as used herein refers to N-Acetylated Alpha-Linked Acidic Dipeptidase. The enzyme was originally named for it's substrate specificity for hydrolyzing N-acetylated alpha-linked acidic dipeptides. Currently, it is known that the enzyme has a broader range of substrate specificity than originally discovered, particularly that the enzyme does not require N-acetylation or alpha-linkage. Thus, as used herein "NAALADase" encompasses other names used in the literature such as NAAG hydrolyzing enzyme and NAALA dipeptidase.

As used in the specification and claims, the chemical structures refer to conventional designations. For example, "alkyl" is a paraffinic hydrocarbon group which may be derived from an alkane by dropping one hydrogen from the formula, and includes but is mot limited to substituents such as methyl, ethyl, propyl, isopropyl, butyl, and so forth. "Alkenyl" is an olefinic unsaturated hydrocarbon having one or more double bonds exemplified by groups such as methylene, ethylene, propylene, isopropylene, butylene, and so forth. The term "Cyclo", used herein as a prefix, refers to a structure characterized by a closed ring. The term "oxy", used herein as a suffix, i.e. alkoxy, alkenoxy, phenoxy, and so forth, refers to having one or more oxygen molecules attached. Thus, the term "carboxy" may describe, for example, a carbon having both an oxygen and a hydroxy moiety attached.

"Halogen" includes bromo, fluoro, chloro and iodo; "halomethyl" includes mono-, di-, and tri-halo groups including trifluoromethyl; amino compounds include amine ($NH_2$) as well as substituted amino groups comprising alkyls of one through six carbons; "$Ar_1$", chemical shorthand for "aryl", includes aromatic ring compounds exemplified by groups such as benzene, phenyl, naphthyl, indolyl, furyl, thienyl, pyridyl, and substituted forms thereof; "aralkyl" is an aryl being attached through an alkyl chain, straight or branched, of from one through six carbons such as phenylpropyl group.

The term "inhibition", in the context of enzyme inhibition, relates to reversible enzyme inhibition such as competitive, uncompetitive, and noncompetitive inhibition. This can be experimentally distinguished by the effects of the inhibitor on the reaction kinetics of the enzyme, which may be analyzed in terms of the basic Michaelis-Menten rate equation. Competitive inhibition occurs when the inhibitor can combine with the free enzyme in such a way that it competes with the normal substrate for binding at the active site. A competitive inhibitor reacts reversibly with the enzyme to form an enzyme-inhibitor complex [EI], analogous to the enzyme-substrate complex:

$$E + I == EI$$

Following the Michaelis-Menten formalism, we can define the inhibitor constant, $K_i$, as the dissociation constant of the enzyme-inhibitor complex:

$$K_i = \frac{[E][I]}{[EI]}$$

Thus, in accordance with the above and as used herein, $K_i$ is essentially a measurement of affinity between a molecule, and its receptor, or in relation to the present invention, between the present inventive compounds and the enzyme to be inhibited. It should be noted that IC50 is a related term used when defining the concentration or amount of a compound which is required to cause a 50% inhibition of the target enzyme.

The term "inhibition", in the context of tumor growth or tumor cell growth, may be assessed by delayed appearance of primary or secondary tumors, slowed development of primary or secondary tumors, decreased occurrence of primary or secondary tumors, slowed or decreased severity of secondary effects of disease, arrested tumor growth and regression of tumors, among others. In the extreme, complete inhibition, is referred to herein as prevention.

The term "prevention", in relation to tumor growth or tumor cell growth, means no tumor or tumor cell growth if none had occurred, no further tumor or tumor cell growth if there had already been growth.

The term "prostate disease" relates to prostate cancer such as adenocarcinoma or metastatic cancers, conditions characterized by abnormal growth of prostatic epithelial cells such as benign prostatic hyperplasia, and other conditions requiring treatment by the compounds of the present invention.

The term "treatment" refers to any process, action, application, therapy, or the like, wherein an animal, including a human being, is subject to medical aid with the object of improving the animal's condition, directly or indirectly.

The compounds and compositions of the present invention useful for treatment of cancer, include but are not limited to types of cancer selected from the following group: ACTH-producing tumors, acute lymphocytic leukemia, acute nonlymphocytic leukemia, cancer of the adrenal cortex, bladder cancer, brain cancer, breast cancer, cervix cancer, chronic lymphocytic leukemia, chronic myelocytic leukemia, colorectal cancer, cutaneous T-cell lymphoma, endometrial cancer, esophageal cancer, Ewing's sarcoma, gallbladder cancer, hairy cell leukemia, head & neck cancer, Hodgkin's lymphoma, Kaposi's sarcoma, kidney cancer, liver cancer, lung cancer(small and/or non-small cell), malignant peritoneal effusion, malignant pleural effusion, melanoma, mesothelioma, multiple myeloma, neuroblastoma, non-Hodgkin's lymphoma, osteosarcoma, ovary cancer, ovary (germ cell) cancer, pancreatic cancer, penis cancer, prostate cancer, retinoblastoma, skin cancer, soft-tissue sarcoma, squamous cell carcinomas, stomach cancer, testicular cancer, thyroid cancer, trophoblastic neoplasms, cancer of the uterus, vaginal cancer, cancer of the vulva, and Wilm's tumor.

Since there is substantial evidence that NAALADase is a metallopeptidase, the present invention includes small molecules with functional groups known to inhibit metallopeptidases, such as hydroxyphosphinyl derivatives, thio derivatives, and hydroxamic acids. The most preferred compounds of the present invention are phosphinic acid derivatives. In particular, since it was known in neurological literature that the glutamate moiety of NAAG was important for recognition by the enzyme and that the aspartate region played a less critical role, a series of glutamate-derived hydroxyphosphinyl derivatives were produced.

As a result, it has been unexpectedly found that compounds with the following general structure were found to be very potent inhibitors of the NAALADase:

These compounds may be prepared by the general method of Jackson et al. (*J. Med. Chem.* 39(2), 619–622; *J. Med. Chem.* 38, 3313–3331). Their synthesis is outlined in Schemes 1, 2, and 3, below.

Synthesis of NAALADase Inhibitors

All of the above-described inhibitors can be synthesized by standard organic synthetic procedures. The precursor compounds of the present invention can be easily made by a ordinary person skill in the art utilizing known methods, such as Scheme 1 below. Production of compounds containing the R group substitutions can be easily made utilizing known methods. See, for example, Froestl et al., *J. Med. Chem.*, 1995, 38, 3313–3331, Phosphinic Acid Analogues of GABA.

Scheme 1

Further methods of synthesizing phosphinic acid esters are also described in *J. Med. Chem.*, 1988, 31, 204–212, and may be found in Scheme II, below.

Scheme II

Method A

A. R' = $(CH_2)_3Ph$  H. n-$C_7H_{15}$
B. $(CH_2)_4Ph$  I. n-$C_8H_{17}$
C. $(CH_2)_5Ph$  J. n-$C_9H_{19}$
D. $(CH_2)_4(P-F-Ph)$  K. n-$C_{10}H_{21}$
E. $(CH_2)_4-(3$-pyridyl$)$  L. $CH_2(CH)(CH_3)C_4H_9$
F. n-$C_5H_{11}$  M. $CH_2(CH_3)CH(CH_3)_2$
G. n-$C_6H_{13}$ Method B N. R' = n-$C_4H_9$
O. $CH(CH_3)C_5H_{11}$ Starting with the aforementioned phosphinic acid esters, there are a variety of routes that can be used to prepare the compounds of the present invention. For example, a general route was recently described in *J. Med. Chem.*, 1996, 39, 619–622, and is set forth below in

SCHEME III

In vitro inhibition of NAALADase Activity

Three compounds were tested for inhibition of NAALADase activity: 2-(phosphonomethyl) pentanedioic acid, 2-(phosphonomethyl)succinic acid, and 2-[[2-carboxyethyl)hydroxyphosphinol]methyl]-pentanedoic acid. The results are shown in Table I.

TABLE I in vitro Activity of NAALADase Inhibitors

| compd | $K_i$ (nM) |
| --- | --- |
| 2-(phosphonomethyl)pentanedioic acid | 0.275 ± 0.08 |
| 2-(phosphonomethyl)succinic acid | 700 ± 67.3 |
| 2-[[2-carboxyethyl)hydroxyphosphinol]methyl]-pentanedoic acid) | 1.89 ± 0.19 |

2-(phosphonomethyl)pentanedioic acid showed a high level of NAALADase inhibiting activity, with a $K_i$ of 0.27 nM (Table 1). The activity of this compound is >1000 times more potent than that of previously described inhibitors. The procedure for assaying the compounds is set forth below.

NAALADase activity was assayed as described. In brief, the assay measured the amount of [$^3$H]Glu liberated from [$^3$H]NAAG in 50 mM Tris-Cl buffer in 15 min at 37° C. using 30–50 μg of synaptosomal protein; substrate and product were resolved by anion-exchange liquid chromatography. Duplicate assays were always performed so that no more than 20% of the NAAG was digested, representing the linear range of peptidase activity. Quisqualate (100 μM) was included in parallel assay tubes to confirm the specificity of measurements.

The 2-(phosphonomethyl)succinic acid showed a large decrease in efficacy in inhibiting the activity of NAALADase (Table 1), suggesting that a glutamate analog attached to the phosphonic acid is required for potent inhibition of the enzyme. In addition, 2-[[2-carboxyethyl) hydroxyphosphinol]methyl]-pentanedoic acid, which has an additional carboxylic acid side chain similar to the aspartate residue found in NAAG, did not lead to an increase in potency.

It is believed that the compounds of the present invention will not tend to be particularly toxic when administered to humans in that NAALADase inhibitors have not demonstrated toxic side effects when administered to rats and mice during in vivo neurological experiments. Furthermore, NAALADase inhibitors have not demonstrated toxic side effects upon exposure to cell lines.

In order to explore the potential toxicological effects of NAALADase inhibition, a group of mice were injected with a single peritoneal dose of 2-(phosphonomethyl) pentanedioic acid, a NAALADase inhibitor having a high activity. The dosages were given in increasing concentrations of milligrams (mg) per kilogram (kg) of body weight. Dosages of 1, 5, 10, 30, 100, 300, and 500 mg/kg (of body weight) were administered and no acute adverse effects were observed at any dose tested. The mice were subsequently observed two times per day for 5 consecutive days. Table II gives the percent survival rate for the doses tested.

TABLE II

NAALADase Inhibitor

| mg/kg | DOSES OF COMPOUND | | | | | | |
| --- | --- | --- | --- | --- | --- | --- | --- |
| | 1 | 5 | 10 | 30 | 100 | 300 | 500 |
| % of animal survival as of Day 5 | 100 | 100 | 100 | 100 | 100 | 100 | 66.7 |

In Vitro Assay of NAALADase Inhibitors on a cancer cell line

Figure 1:
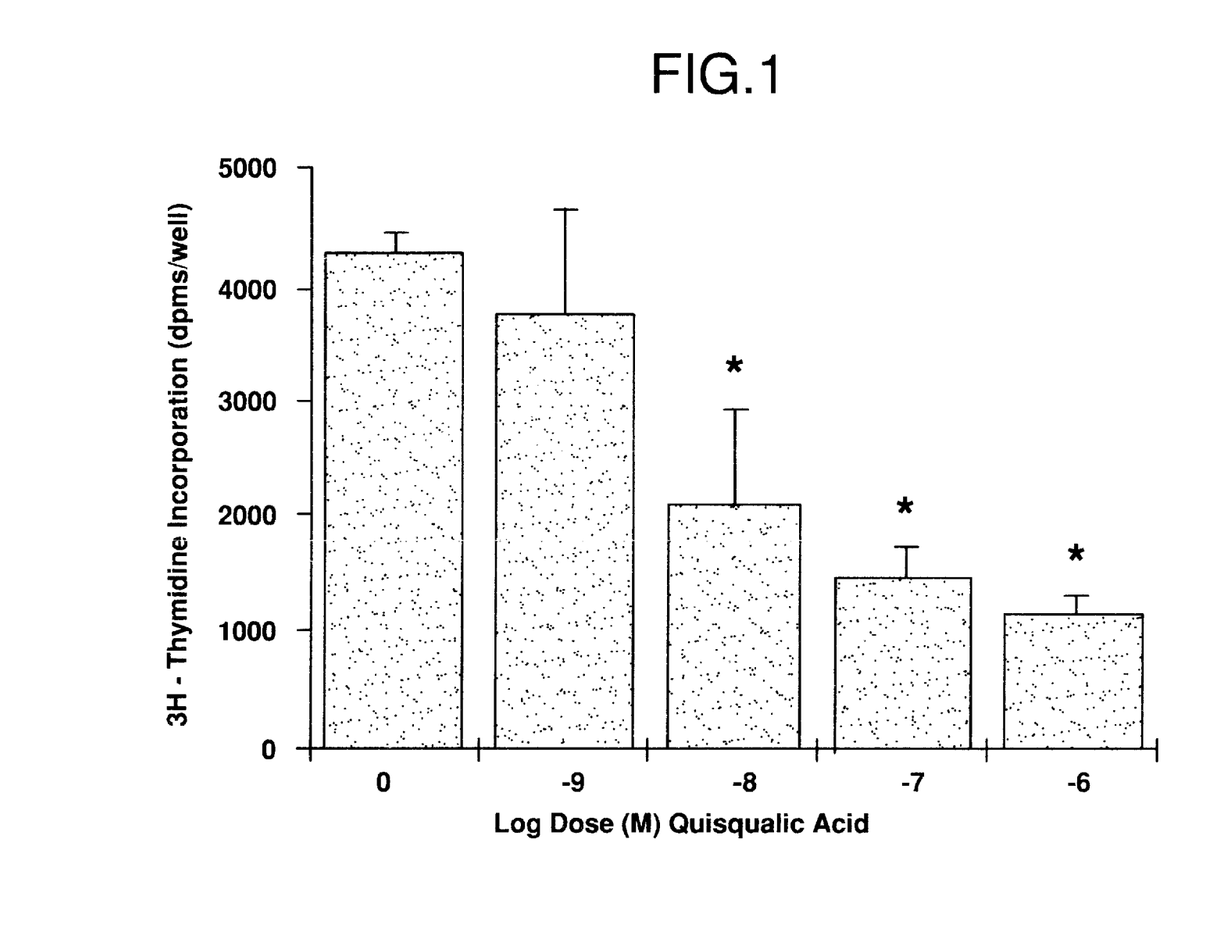
FIG. 1 is a bar graph plotting the growth of the prostate cancer cell line, LNCAP, against various concentrations of quisqualic acid.
Figure 2:
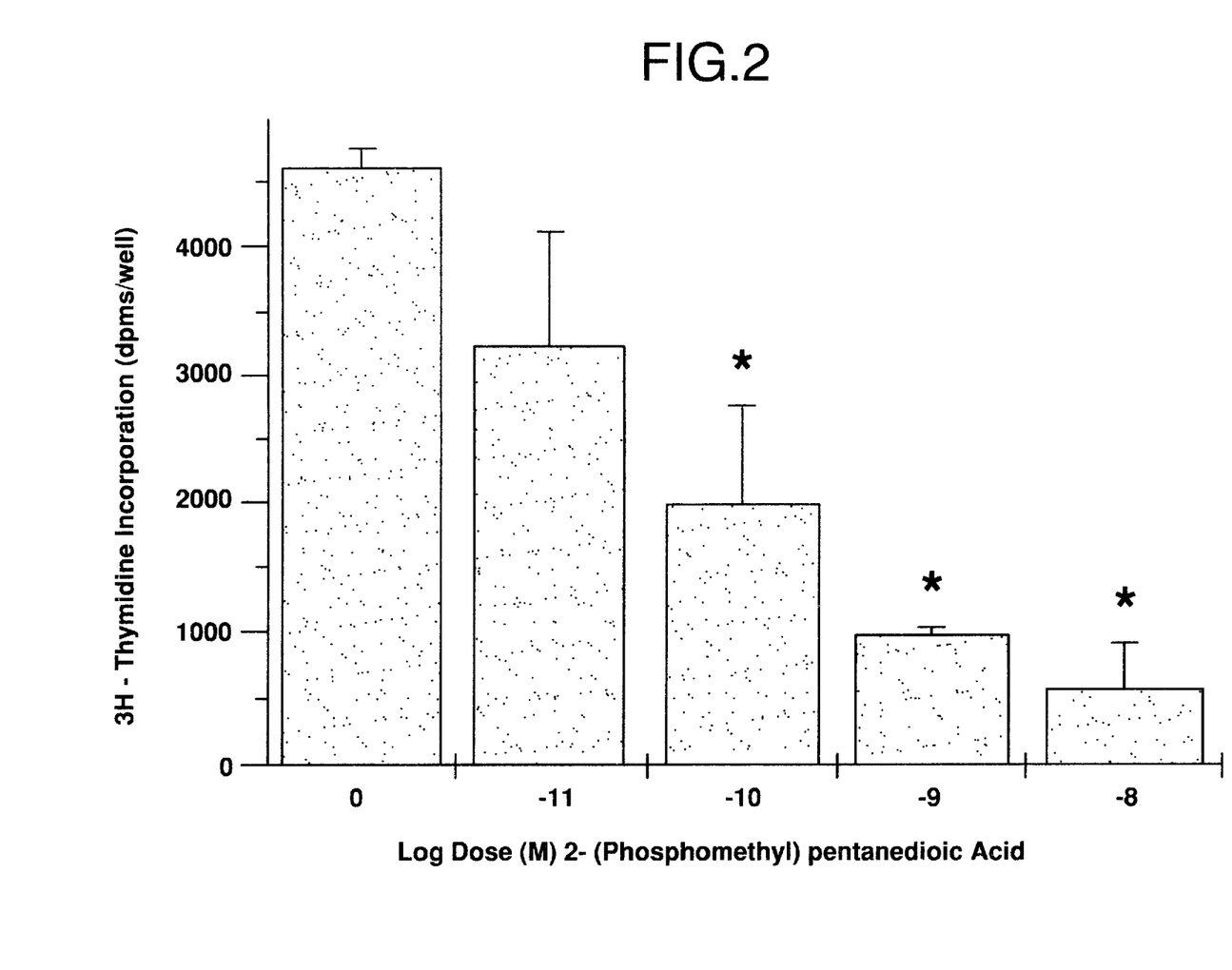
FIG. 2 is a bar graph plotting the growth of the prostate cancer cell line, LNCAP, against various concentrations of 2-(phosphonomethyl)pentanedioic acid.

Referring now to FIGS. 1 and 2 of the drawings, the effect of 7-day treatment with quisqualate and 2-(phosphonomethyl)pentanedioic acid on the growth of LNCAP cells (a prostate cancer cell line) is shown in FIGS. 1 and 2, respectively. Concentrations ranging from 10 nM to 1 μM of quisqualate and 100 pM to 10 nM of 2-(phosphonomethyl)pentanedioic acid show a sharp dose-dependent decrease of LNCAP cell proliferation as indicated by the significant decrease in the incorporation of [3H] thymidine. The data for FIGS. 1 and 2 is shown in Table III, below.

TABLE III $^3$H-Thymidine Incorporation (DPMs)

| Dose | Quisqualic Acid | 2(phosphonomethyl) pentanedioic Acid |
| --- | --- | --- |
| Control | 4813 ± 572 | 4299 ± 887 |
| 10 pM | — | 3078 ± 1006 |
| 100 pM | — | 2062 ± 595 |
| 1 nM | 3668 ± 866 | 1001 ± 52 |
| 10 nM | 2137 ± 764 | 664 ± 366 |
| 100 nM | 1543 ± 312 | — |
| 1 uM | 1295 ± 181 | — |

The data for Table III was obtained according to the following protocol. Cells in RPMI 1640 medium containing 10% Fetal Calf Serum (FCS) were plated in 24 well plates and were allowed to adhere for 24 hours before addition of quisqualic acid ($10^{-9}$ to $10^{-6}$) or 2-(phosphonomethyl) pentanedioic acid ($10^{-1}$ to $10^{-8}$) for 7 days. On the 7th day, the cells were pulsed with 3H-Thymidine for 4 hours, harvested and radioactivity was measured. Values represent means +/− SEM of G separate cell wells for each treatment. All experiments were performed at least twice.

To control for the non-specific cytostatic effects of these NAALADase inhibitors, the effects of these agents were simultaneously evaluated on the non-NAALADase containing prostate cell line, DU145 (Carter et al., Proc. Natl. Acad. Sci. USA, (93) 749–753; 1996). The effect of 7-day treatment of quisqualate and 2-(phosphonomethyl)pentanedioic acid at concentrations up to μM had no significant effect on cell growth. These observations provide evidence that the NAALADase inhibition properties of these agents are uniquely responsible for their cytostatic effects on prostate carcinoma cell lines.

Cell Lines and Tissue Culture

LNCAP cells were obtained from Dr. William Nelson at the Johns Hopkins School of Medicine in Baltimore, Md. DU145 cells were obtained from American Type Culture Collection (Rockville, Md.). Cells were grown in RPMI-1640 media supplemented with 5% heat-inactivated fetal calf serum, 2 mM-glutamine, 100 units/ml penicillin, and 100 μg/ml streptomycin (Paragon) in a humidified incubator at 37° C. in a 5% $CO_2$/95% air atmosphere.

[3H] Thymidine Incorporation Assays

The cells were suspended at 1×10$^3$ cells/ml in RPMI-1640 media and seeded into 24-well plates at 500 μl per well. After 24 hour incubation, various concentrations of quisqualic acid (Sigma) or the potent NAALADase inhibitor 2-(phosphonomethyl)pentanedioic acid (synthesized according to the methods of Jackson et al., J. Med. Chem. 39(2) 619–622) was added to the wells and the plates were returned to the incubator. On days 3, 5, and 7, media and drug were refreshed. On the 8th day following seeding, each well was pulsed with 1 μCi $^3$H-thymidine (New England Nuclear) for 4 hours. Media was then removed and the wells washed 2 times with phosphate buffered saline (pH=7.4). The contents of each well was subsequently solubilized 250 μl of 0.2N NaOH and transferred to scintillation vials. Five mls of UltimaGold (Packard) scintillation cocktail was added and radioactivity was quantitated using a Beckman LS6001 scintillation counter.

The purity and/or identity of all synthetic compounds is ascertained by thin layer chromatography, High Pressure Liquid Chromatography (HPLC), mass spectrometry, and elemental analysis. Proton Nuclear Magnetic Resonance (NMR) spectra were obtained using a Bruker spectrometer. Chemical shifts are reported in parts per million relative to tetramethylsilane as internal standard. Analytical thin-layer chromatography (TLC) was conducted on prelayered silica gel GHLF plates (Analtech, Newark, Del.). Visualization of the plates was accomplished by using UV light, phosphomolybdic acid-ethanol, and/or iodoplatinate charring. Flash chromatography was conducted on Kieselgel 60, 230–400 mesh (E. Merck, Darmstadt, West Germany). Solvents were either reagent or HPLC grade. Reactions were run at ambient temperature and under a nitrogen atmosphere unless otherwise noted. Solutions were evaporated under reduced pressure on a Buchi rotary evaporator.

The compounds of the present invention can be used in the form of salts derived from inorganic or organic acids and bases. Included among such acid salts are the following: acetate, adipate, alginate, aspartate, benzoate, benzenesulfonate, bisulfate butyrate, citrate, camphorate, camphorsulfonate, cyclopentanepropionate, digluconate, dodecylsulfate, ethanesulfonate, fumarate, glucoheptanoate, glycerophosphate, hemissulfate heptanoate, hexanoate, hydrochloride, hydrobromide, hydroiodide, 2-hydroxyethanesulfonate, lactate, maleate, methanesulfonate, 2-naphthalensulfonate, nicotinate, oxalate, pamoate, pectinate, propionate, succinate, tartrate, thiocyanate, tosylate and undecanoate. Base salts include ammonium salts, alkali metal salts such as sodium and potassium salts, alkaline earth metal salts such as calcium and magnesium salts, salt with organic bases such as dicyclohexylamine salts, N-methyl-D-glucamine, and salts with amino acids such as arginine, lysine, and so forth. Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl and diamyl sulfates, long chain halides such as decyl, lauryl, myristyl and stearyl chlorides, bromides and iodides, aralkyl halides like benzyl and phenethyl bromides and others. Water or oil-soluble or dispersible products are thereby obtained.

ROUTE OF ADMINISTRATION

For these purposes, the compounds of the present invention may be administered orally, parenterally, by inhalation spray, topically, rectally, nasally, buccally, vaginally or via an implanted reservoir in dosage formulations containing conventional non-toxic pharmaceutically-acceptable carriers, adjuvants and vehicles. The term parenteral as used herein includes subcutaneous, intravenous, intramuscular, intraperitoneally, intrathecally, intraventricularly, intrasternal and intracranial injection or infusion techniques. Generally, at the present time, invasive techniques are preferred, particularly administration directly into tumors.

In addition, administration may be by a single dose, it may be repeated at intervals or it may be by continuous infusion. Where continuous infusion is preferred, pump means often will be particularly preferred for administration. Especially, subcutaneous pump means may be preferred in this regards.

Since NAALADase inhibitors are small, easily diffusible, and relatively stable, it is well suited to long-term continuous administration, such as by a perfusion pump. Also, it may be desirable to administer NAALADase inhibitors and other agents of the present invention by intraperitoneal injection on a regular basis.

Compositions and methods of the invention also may utilize controlled release technology. Thus, for example, NAALADase inhibitors may be incorporated into a hydrophobic polymer matrix for controlled release over a period of days. Such controlled release films are well known to the art. Examples of polymers commonly employed for this purpose that may be used in the present invention include nondegradable ethylene-vinyl acetate copolymer and degradable lactic acid-glycolic acid copolymers. Certain hydrogels such as poly(hydroxyethylmethacrylate) or poly (vinylalcohol) also may be useful, but for shorter release cycles then the other polymer releases systems, such as those mentioned above.

To be effective therapeutically and avoid unwanted neurological effects which may or may not be caused by NAALADase inhibitors in neural tissue, the composition should be formulated such that it will not readily penetrate the blood-brain barrier in significant amounts when peripherally administered. However, for compositions which are administered locally, such by intraperitoneal injection or by polymeric implant, such neurological concerns may be obviated.

The pharmaceutical compositions may be in the form of a sterile injectable preparation, for example as a sterile injectable aqueous or oleaginous suspension. This suspension may be formulated according to techniques know in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. Fatty acids such as oleic acid and its glyceride derivatives find use in the preparation of injectables, olive oil or castor oil, especially in their polyoxyethylated versions. These oil solutions or suspensions may also contain a long-chain alcohol diluent or dispersant.

The compounds may be administered orally in the form of capsules or tablets, for example, or as an aqueous suspension or solution. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening and/or flavoring and/or coloring agents may be added.

The compounds of this invention may also be administered in the form of suppositories for rectal administration of the drug. These compositions can be prepared by mixing the drug with a suitable non-irritating excipient which is solid at room temperature but liquid at rectal temperature and therefore will melt in the rectum to release the drug. Such materials include cocoa butter, beeswax and polyethylene glycols.

The compounds of this invention may also be administered optically, especially when the conditions addressed for treatment involve areas or organs readily accessible by topical application, including neurological disorders of the eye, the skin, or the lower intestinal tract. Suitable topical formulations are readily prepared for each of these areas. For ophthalmic use, the compounds can be formulated as micronized suspensions in isotonic, pH adjusted sterile saline, or, preferably, as solutions is isotonic, pH adjusted sterile saline, either with or without a preservative such as benzylalkonium chloride. Alternatively for the ophthalmic uses the compounds may be formulated in an s ointment such as petrolatum.

For application topically to the skin, the compounds can be formulated in a suitable ointment containing the compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, the compounds can be formulated in a suitable lotion or cream containing the active compound suspended or dissolved in, for example, a mixture of one or more of the following: mineral oil, sorbitan monostearate, polysorbate 60, cetyl esters wax, cetearyl alcohol, 2-octyldodecanol, benzyl alcohol and water.

Topical application for the lower intestinal tract may be effected in a rectal suppository formulation (see above) or in a suitable enema formulation.

DOSE

Dosage levels on the order of about 0.1 mg to about 10,000 mg of the active ingredient compound are useful in the treatment of the above conditions, with preferred levels of about 0.1 mg to about 1,000 mg. The amount of active ingredient that may be combined with the carrier materials to produce a single dosage form will vary depending upon the host treated and the particular mode of administration.

It is understood, however, that a specific dose level for any particular patient will depend upon a variety of factors including the activity of the specific compound employed, the age, body weight, general health, sex, diet, time of administration, rate of excretion, drug combination, and the severity of the particular disease being treated and form of administration.

Treatment dosages generally may be titrated to optimize safety and efficacy. Typically, dosage-effect relationships from in vitro initially can provide useful guidance on the proper doses for patient administration. Studies in animal models also generally may be used for guidance regarding effective dosages for treatment of cancers in accordance with the present invention. In terms of treatment protocols, it should be appreciated that the dosage to be administered will depend on several factors, including the particular analog that is administered, the route administered, the condition of the particular patient, etc. In that most of these agents have peptidyl portions it will generally be desirable to administer the agents I.V., but administration by other routes is contemplated where appropriate. Generally speaking, one will desire to administer an amount of the agent that is effective to achieve a serum level commensurate with the concentrations found to be effective in vitro. Thus, where an agent is found to demonstrate in vitro activity at, e.g., 10 $\mu$M, one will desire to administer an amount of the drug that is effective to provide about a 10 $\mu$M concentration in vivo. Determination of these parameters are well within the skill of the art.

These considerations, as well as effective formulations and administration procedures are well known in the art and are described in standard textbooks.

A particular formulation of the invention uses a lyophilized form of NAALADase inhibitor, in accordance with well known techniques. For instance, 1 to 100 mg of NAALADase inhibitor may be lyophilized in individual vials, together with carrier and buffer compound, for instance, such as mannitol and sodium phosphate. The NAALADase inhibitor may be reconstituted in the vials with bacteriostatic water and then administered, as described elsewhere herein.

ADMINISTRATION REGIMEN

Any effective treatment regimen can be utilized and readily determined and repeated as necessary to effect treatment.

In clinical practice, the compositions containing NAALADase inhibitor alone or in combination with other therapeutic agents are administered in specific cycles until a response is obtained.

For patients who initially present without advanced or metastatic cancer, NAALADase inhibitor based drugs are used as an immediate initial therapy prior to surgery and radiation therapy, and as a continuous post-treatment therapy in patients at risk for recurrence or metastasis (based upon high PSA, high Gleason's score, locally extensive disease, and/or pathological evidence of tumor invasion in the surgical specimen). The goal in these patients is to inhibit the growth of potentially metastatic cells from the primary tumor during surgery or radiotherapy and inhibit the growth of tumor cells from undetectable residual primary tumor.

For patients who initially present with advanced or metastatic cancer, NAALADase inhibitor based drugs are used as a continuous supplement to, or possible as a replacement for hormonal ablation. The goal in these patients is to slow tumor cell growth from both the untreated primary tumor and from the existing metastatic lesions.

In addition, the invention may be particularly efficacious during post-surgical recovery, where the present compositions and methods may be particularly effective in lessening the chances of recurrence of a tumor engendered by shed cells that cannot be removed by surgical intervention.

COMBINATION WITH OTHER TREATMENTS

NAALADase inhibitor may be used in conjunction with other treatment modalities. Other common treatment modalities are discussed below specifically by reference to prostate cancer. It will be appreciated that similar consideration will apply to treatment of other metastatic cancers. The present invention may be used in conjunction with any current or future therapy.

Surgery and Radiation

In general, surgery and radiation therapy are employed as potentially curative therapies for patients under 70 years of age who present with clinically localized disease and are expected to live at least 10 years.

Approximately 70% of newly diagnosed prostate cancer patients fall into this category. Approximately 90% of these patients (65% of total patients) undergo surgery, while approximately 10% of these patients (7% of total patients) undergo radiation therapy.

Histopathological examination of surgical specimens reveals that approximately 63% of patients undergoing surgery (40% of total patients) have locally extensive tumors or regional (lymph node)metastasis that was undetected at initial diagnosis. These patients are at a significantly greater risk of recurrence. Approximately 40% of these patients will actually develop recurrence within five years after surgery. Results after radiation are even less encouraging. Approximately 80% of patients who have undergone radiation as their primary therapy have disease persistence or develop recurrence or metastasis within five years after treatment.

Currently, most of these surgical and radiotherapy patients generally do not receive any immediate follow-up therapy. Rather, they are monitored frequently for elevated Prostate Specific Antigen ("PSA"), which is the primary indicator of recurrence or metastasis.

Thus, there is considerable opportunity to use the present invention in conjunction with surgical intervention.

Hormonal Therapy

Hormonal ablation is the most effective palliative treatment for the 10% of patients presenting with metastatic prostate cancer at initial diagnosis. Hormonal ablation by medication and/or orchiectomy is used to block hormones that support the further growth and metastasis of prostate cancer. With time, both the primary and metastatic tumors of virtually all of these patients become hormone-independent and resistant to therapy. Approximately 50% of patients presenting with metastatic disease die within three years after initial diagnosis, and 75% of such patients die within five years after diagnosis. Continuous supplementation with NAALADase inhibitor based drugs are used to prevent or reverse this potentially metastasis-permissive state.

Chemotherapy

Chemotherapy has been more successful with some cancers than with others. It is likely that the combination of chemotherapy with therapies of the present invention in some cases will be synergistic. However, chemotherapy currently has little effect on prostate cancer and is generally reserved as a last resort, with dismal results. For this type of cancer, the opportunity to combine chemotherapy with methods and compositions of the invention will be rare.

Immunotherapy

The NAALADase inhibitors may also be used in combination with monoclonal antibodies in treating prostate cancer. Because pelvic lymph node involvement affects the 5-year survival rate—84% of patients without pelvic lymph node involvement survive 5 years, compared with only 34% of those having pelvic lymph node involvement, the use of NAALADase inhibitors in combination with monoclonal antibodies becomes significant. A specific example of such an antibody includes cell membrane-specific anti-prostate antibody.

The present invention may also be used with immunotherapies based on polyclonal or monoclonal antibody-derived reagents, for instance. Monoclonal antibody-based reagents are most preferred in this regard. Such reagents are well known to persons of ordinary skill in the art. Radiolabelled monoclonal antibodies for cancer therapy, such as the recently approved use of monoclonal antibody conjugated with strontium-89, also are well known to persons of ordinary skill in the art.

Cryotherapy

Cryotherapy recently has been applied to the treatment of some cancers. Methods and compositions of the present invention also could be used in conjunction with an effective therapy of this type.

COMBINATIONS WITH OTHER ACTIVE AGENTS

According to another aspect of the invention, pharmaceutical compositions of matter useful for inhibiting cancer are provided that contain, in addition to the aforementioned compounds, an additional therapeutic agent. Such agents may be chemotherapeutic agents, ablation or other therapeutic hormones, antineoplastic agents, monoclonal antibodies useful against cancers and angiogenesis inhibitors. The following discussion highlights some agents in this respect, which are illustrative, not limitative. A wide variety of other effective agents also may be used.

Among hormones which may be used in combination with the present inventive compounds, diethylstilbestrol (DES), leuprolide, flutamide, cyproterone acetate, ketoconazole and amino glutethimide are preferred.

Among antineoplastic and anticancer agents that may be used in combination with the inventive compounds, 5-fluorouracil, vinblastine sulfate, estramustine phosphate, suramin and strontium-89 are preferred. Other chemotherapeutics useful in combination and within the scope of the present invention are buserelin, chlorotranisene, chromic phosphate, cisplatin, cyclophosphamide, dexamethasone, doxorubicin, estradiol, estradiol valerate, estrogens conjugated and esterified, estrone, ethinyl estradiol, floxuridine, goserelin, hydroxyurea, melphalan, methotrexate, mitomycin and prednisone.

Table IV provides known median dosages for selected cancer agents which may be useful in combination with the compounds and compositions of the present invention. It should be noted that specific dose levels for the chemotherapeutic agents below will depend upon similar dosing considerations as those listed in the DOSAGE section for NAALADase inhibitors presented herein.

TABLE IV

| NAME OF CHEMOTHERAPEUTIC AGENT | MEDIAN DOSAGE |
| --- | --- |
| Asparaginase | 10,000 units |
| Bleomycin Sulfate | 15 units |
| Carboplatin | 50–450 mg. |
| Carmustine | 100 mg. |
| Cisplatin | 10–50 mg. |
| Cladribine | 10 mg. |
| Cyclophosphamide (lyophilized) | 100 mg.–2 gm. |
| Cyclophosphamide (non-lyophilized) | 100 mg.–2 gm. |
| Cytarabine (lyophilized powder) | 100 mg.–2 gm. |
| Dacarbazine | 100 mg.–200 mg. |
| Dactinomycin | 0.5 mg. |
| Daunorubicin | 20 mg. |
| Diethylstilbestrol | 250 mg. |
| Doxorubicin | 10–150 mg. |
| Etidronate | 300 mg. |
| Etoposide | 100 mg. |
| Floxuridine | 500 mg. |
| Fludarabine Phosphate | 50 mg. |
| Fluorouracil | 500 mg.–5 gm. |
| Goserelin | 3.6 mg. |
| Granisetron Hydrochloride | 1 mg. |
| Idarubicin | 5–10 mg. |
| Ifosfamide | 1–3 gm. |
| Leucovorin Calcium | 50–350 mg. |
| Leuprolide | 3.75–7.5 mg. |

TABLE IV-continued

| NAME OF CHEMOTHERAPEUTIC AGENT | MEDIAN DOSAGE |
| --- | --- |
| Mechlorethamine | 10 mg. |
| Medroxyprogesterone | 1 gm. |
| Melphalan | 50 gm. |
| Methotrexate | 20 mg.–1 gm. |
| Mitomycin | 5–40 mg. |
| Mitoxantrone | 20–30 mg. |
| Ondansetron Hydrochloride | 40 mg. |
| Paclitaxel | 30 mg. |
| Pamidronate Disodium | 30–*90 mg. |
| Pegaspargase | 750 units |
| Plicamycin | 2,500 mcgm. |
| Streptozocin | 1 gm. |
| Thiotepa | 15 mg. |
| Teniposide | 50 mg. |
| Vinblastine | 10 mg. |
| Vincristine | 1–5 mg. |
| Aldesleukin | 22 million units |
| Epoetin Alfa | 2,000–10,000 units |
| Filgrastim | 300–480 mcgm. |
| Immune Globulin | 500 mg.–10 gm. |
| Interferon Alpha-2a | 3–36 million units |
| Interferon Alpha-2b | 3–50 million units |
| Levamisole | 50 mg. |
| Octreotide | 1,000–5,000 mcgm. |
| Sargramostim | 250–500 mcgm. |

The following examples are illustrative of preferred embodiments of methods of preparation of compounds of the invention and are not to be construed as limiting the invention thereto. Unless otherwise indicated, all percentages are based upon 100% of the final formulations.

EXAMPLE 1

This example demonstrates the preparation of Dibenzyl 2-Methylenepentanedioate using Scheme III.

Benzyl acrylate (19.4 g, 120 mmol) was cooled in a two neck 250 ml round bottom flask to approximately 5° C. To this was added dropwise HMPT (2.14 g, 133.1 mmol) at such a rate as to maintain a temperature of 5°–10° C. Once addition was complete the ice/water bath was removed and the mixture allowed to warm to room temperature. Stirring was continued overnight. The clear yellow liquid was added directly to a silica gel column (4 cm*40 cm) and eluted with a gradient (19:1–9:1) solvent system (hexane/EtOAc). The fractions containing the desired material were combined and evaporated to give 1 (10.1 g, 52%) as a clear and colorless liquid. TLC $R_f$ 0.26 (9:1, Hex./EtOAc).
1H-NMR (CDCl3)
7.2–7.3 (m, 10H); 6.15 (s, 1H); 5.55 (s, 1H); 5.12 (s, 2H); 5.08 (s,2H); 2.58–2.68 (m, 2H); 2.48–2.55 (m, 2H).

EXAMPLE 2

This example demonstrates the preparation of Dibenzyl 2-[[Bis(benzyloxy)phosphoryl]methyl]-pentanedioate using Scheme III.

Dibenzyl phosphite (9.5 g, 36 mmol) in 350 ml of dichloromethane was cooled to 0° C. To this stirring solution was added trimethyl aluminum (18.2 ml, 2.0M solution in hexane, 36.4 mmol). After 30 minutes 1 (6.0 g, 37 mmol) in 90 ml of dichloromethane was added dropwise over 10 minutes. The clear and colorless solution was then warmed to room temperature and left to stir overnight. The mixture was then quenched by the slow addition of 5% HCl. After stirring an additional 1.5 hours the lower organic layer was removed and the aqueous layer extracted once with 100 ml of dichloromethane. The organics were combined, dried (MgSO$_4$), and evaporated to give a clear light golden liquid. The liquid was chromatographed on silica gel (4 cm*30 cm) and eluted with a gradient (4:1–1:1) solvent system (Hexane/EtOAc). The fractions containing the desired product were combined and evaporated to yield 2 (7.1 g, 42%) as a clear and colorless liquid. The liquid was then distilled on a Kughleror apparatus at 0.5 mm Hg and 195°–200° C. The distillate was discarded and the remaining light golden oil was chromatographed on silica gel (1:1, Hex./EtOAc) to give 2.9 g of 2 as a clear and colorless oil. TLC $R_f$ 0.5 (1:1, Hex./EtOAc).
1H-NMR (CDCl$_3$)
7.1–7.4 (m, 20H); 5.05 (s, 2H); 4.8–5.03 (m, 6H); 2.8 (1H); 2.22–2.40 (m, 3H); 1.80–2.02 (m, 3H).

EXAMPLE 3

This example demonstrates the preparation of 2-(Phosphonomethyl)pentanedioic Acid using Scheme III.

The benzyl pentanedioate 2(2.9 g, 4.9 mmol) was added to a mixture of 20 ml of methanol containing 0.29 g (6 mol %) of 10% Pd/C. This mixture was hydrogenated on a Parr hydrogenator at 40 psi for 24 hours, filtered and evaporated to give 3(1.0 g, 90%) as a clear slightly golden viscous oil.
1H-NMR (D$_2$O)
2.6–2.78(m, 1H); 2.25–2.40(m, 2H); 1.75–2.15(m, 4H).

EXAMPLE 4

A patient is diagnosed with adenocarcinoma of the prostate. The patient may then be administered a NAALADase inhibitor, such as set forth in examples 1 through 3, by direct injection into the tumor. After this initial treatment, the patient may be optionally administered the same or different NAALADase inhibitor by intermittent or continuous administration by subdural pump. It would be expected that no further occurrences of the adenocarcinoma would develop.

EXAMPLE 5

A patient is diagnosed with adenocarcinoma of the prostate. The patient may then be administered a NAALADase inhibitor, such as set forth in examples 1 through 3, by direct injection into the tumor. After this initial treatment, the patient may be optionally administered the same or different NAALADase inhibitor by intermittent or continuous administration by implantation of a biocompatible, polymeric matrix delivery system. It would be expected that no further occurrences of the adenocarcinoma would develop.

EXAMPLE 6

A patient is diagnosed with benign prostatic hyperplasia. The patient may then be administered a NAALADase inhibitor, such as set forth in examples 1 through 3, by direct injection into the tumor. After this initial treatment, the patient may be optionally administered the same or different NAALADase inhibitor by intermittent or continuous administration by injection, subdural pump, or polymeric matrix implant. It would be expected that the benign prostatic hyperplastic cells do not develop into carcinoma.

EXAMPLE 7

A patient is diagnosed with adenocarcinoma of the prostate. The adenocarcinoma appears not to have metastasized. The adenocarcinoma would be removed by surgery. After post-operative recovery, the patient would be locally administered NAALADase inhibitor by intermittent or continuous administration by injection, subdural pump or by polymeric matrix implant. It would expected that no further occurrences of the carcinoma would develop.

EXAMPLE 8

A patient is diagnosed with metastatic adenocarcinoma of the prostate. The adenocarcinoma appears to have metastasized, but surgery still is indicated as an effective treatment modality. Tumor tissue would be removed by surgery. The patient would be locally administered a NAALADase inhibitor such as described herein from the time, approximately, of the initial diagnosis and would continue after surgery. After post-operative recovery, the patient would be maintained at this level of NAALADase inhibitor by a regimen of periodic local administration. The patient would be monitored carefully for intolerable adverse side-effects of NAALADase inhibitor administration. It would be expected that no further tumors develop. If some of the original, small tumorous masses are detected after surgery, they would be expected to not grow in size.

EXAMPLE 9

A patient is diagnosed with a disorder requiring the administration of a NAALADase inhibitor. The patient may then be administered a NAALADase inhibitor, such as set forth in examples 1 through 3, by direct injection. After this initial treatment, the patient may be optionally administered the same or different NAALADase inhibitor by direct injection, subdural pump, or implantation of a biocompatible, polymeric matrix delivery system. It would be expected that the treatment would alleviate the disorder, either in part or in its entirety and that no further occurrences of the disorder would develop.

EXAMPLE 10

A patient is diagnosed with ACTH-producing tumors. The patient may then be administered a NAALADase inhibitor, such as set forth in examples 1 through 3, by direct injection into the tumor. After this initial treatment, the patient may be optionally administered the same or different NAALADase inhibitor by direct injection, subdural pump, or implantation of a biocompatible, polymeric matrix delivery system. It would be expected that tumor growth or tumor cell growth would be prevented or inhibited and that no further occurrences of the ACTH-producing tumor would develop.

EXAMPLE 11

A treatment such as that described in Example 9 wherein the patient is diagnosed with acute lymphocytic leukemia.

EXAMPLE 12

A treatment such as that described in Example 9 wherein the patient is diagnosed with acute non-lymphocytic leukemia.

EXAMPLE 13

A treatment such as that described in Example 9 wherein the patient is diagnosed with metastatic or non-metastatic cancer of the adrenal cortex.

EXAMPLE 14

A treatment such as that described in Example 9 wherein the patient is diagnosed with metastatic or non-metastatic bladder cancer.

EXAMPLE 15

A treatment such as that described in Example 9 wherein the patient is diagnosed with metastatic or non-metastatic brain cancer.

EXAMPLE 16

A treatment such as that described in Example 9 wherein the patient is diagnosed with metastatic or non-metastatic breast cancer.

EXAMPLE 17

A treatment such as that described in Example 9 wherein the patient is diagnosed with metastatic or non-metastatic cervical cancer.

EXAMPLE 18

A treatment such as that described in Example 9 wherein the patient is diagnosed with metastatic or non-metastatic chronic lymphocytic leukemia.

EXAMPLE 19

A treatment such as that described in Example 9 wherein the patient is diagnosed with metastatic or non-metastatic chronic myelocytic leukemia.

EXAMPLE 20

A treatment such as that described in Example 9 wherein the patient is diagnosed with metastatic or non-metastatic colorectal cancer.

EXAMPLE 21

A treatment such as that described in Example 9 wherein the patient is diagnosed with metastatic or non-metastatic cutaneous T-cell lymphoma.

EXAMPLE 22

A treatment such as that described in Example 9 wherein the patient is diagnosed with metastatic or non-metastatic endometrial cancer.

EXAMPLE 23

A treatment such as that described in Example 9 wherein the patient is diagnosed with metastatic or non-metastatic esophageal cancer.

EXAMPLE 24

A treatment such as that described in Example 9 wherein the patient is diagnosed with metastatic or non-metastatic Ewing's sarcoma.

EXAMPLE 25

A treatment such as that described in Example 9 wherein the patient is diagnosed with metastatic or non-metastatic gallbaldder cancer.

EXAMPLE 26

A treatment such as that described in Example 9 wherein the patient is diagnosed with metastatic or non-metastatic hairy cell leukemia.

EXAMPLE 27

A treatment such as that described in Example 9 wherein the patient is diagnosed with metastatic or non-metastatic head and neck cancer.

EXAMPLE 28

A treatment such as that described in Example 9 wherein the patient is diagnosed with metastatic or non-metastatic Hodgin's lymphoma.

EXAMPLE 29

A treatment such as that described in Example 9 wherein the patient is diagnosed with metastatic or non-metastatic Kaposi's sarcoma.

EXAMPLE 30

A treatment such as that described in Example 9 wherein the patient is diagnosed with metastatic or non-metastatic kidney cancer.

EXAMPLE 31

A treatment such as that described in Example 9 wherein the patient is diagnosed with metastatic or non-metastatic liver cancer.

EXAMPLE 32

A treatment such as that described in Example 9 wherein the patient is diagnosed with metastatic or non-metastatic lung cancer (small cell and/or non-small cell).

EXAMPLE 33

A treatment such as that described in Example 9 wherein the patient is diagnosed with metastatic or non-metastatic malignant peritoneal effusion.

EXAMPLE 34

A treatment such as that described in Example 9 wherein the patient is diagnosed with metastatic or non-metastatic malignant pleural effusion.

EXAMPLE 35

A treatment such as that described in Example 9 wherein the patient is diagnosed with metastatic or non-metastatic melanoma.

EXAMPLE 36

A treatment such as that described in Example 9 wherein the patient is diagnosed with metastatic or non-metastatic mesothelioma.

EXAMPLE 37

A treatment such as that described in Example 9 wherein the patient is diagnosed with metastatic or non-metastatic multiple myeloma.

EXAMPLE 38

A treatment such as that described in Example 9 wherein the patient is diagnosed with metastatic or non-metastatic neuroblastoma.

EXAMPLE 39

A treatment such as that described in Example 9 wherein the patient is diagnosed with metastatic or non-metastatic non-Hodgkin's lymphoma.

EXAMPLE 40

A treatment such as that described in Example 9 wherein the patient is diagnosed with metastatic or non-metastatic osteosarcoma.

EXAMPLE 41

A treatment such as that described in Example 9 wherein the patient is diagnosed with metastatic or non-metastatic ovarian cancer (and/or germ cell ovarian cancer).

EXAMPLE 42

A treatment such as that described in Example 9 wherein the patient is diagnosed with metastatic or non-metastatic pancreatic cancer.

EXAMPLE 43

A treatment such as that described in Example 9 wherein the patient is diagnosed with metastatic or non-metastatic penis cancer.

EXAMPLE 44

A treatment such as that described in Example 9 wherein the patient is diagnosed with metastatic or non-metastatic retinoblastoma.

EXAMPLE 45

A treatment such as that described in Example 9 wherein the patient is diagnosed with metastatic or non-metastatic skin cancer.

EXAMPLE 46

A treatment such as that described in Example 9 wherein the patient is diagnosed with metastatic or non-metastatic soft-tissue sarcoma.

EXAMPLE 47

A treatment such as that described in Example 9 wherein the patient is diagnosed with metastatic or non-metastatic squamous cell carcinoma.

EXAMPLE 48

A treatment such as that described in Example 9 wherein the patient is diagnosed with metastatic or non-metastatic stomach cancer.

EXAMPLE 49

A treatment such as that described in Example 9 wherein the patient is diagnosed with metastatic or non-metastatic testicular cancer.

EXAMPLE 50

A treatment such as that described in Example 9 wherein the patient is diagnosed with metastatic or non-metastatic thyroid cancer.

EXAMPLE 51

A treatment such as that described in Example 9 wherein the patient is diagnosed with metastatic or non-metastatic trophoblastic neoplasm.

EXAMPLE 52

A treatment such as that described in Example 9 wherein the patient is diagnosed with metastatic or non-metastatic uterine cancer.

EXAMPLE 53

A treatment such as that described in Example 9 wherein the patient is diagnosed with metastatic or non-metastatic vaginal cancer.

EXAMPLE 54

A treatment such as that described in Example 9 wherein the patient is diagnosed with metastatic or non-metastatic cancer of the vulva.

EXAMPLE 55

A treatment such as that described in Example 9 wherein the patient is diagnosed with metastatic or non-metastatic Wilm's tumor.

The invention being thus described, it will be obvious that the same may be varied in many ways. Such variations are not to be regarded as a departure from the spirit and scope of the invention and all such modification are intended to be included within the scope of the following claims.

What is claimed is:

1. A pharmaceutical composition which comprises:

i) an effective amount of a compound having the formula:

where

R is a $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, phenyl, 1-napthyl, 2-napthyl, and phenyl ($C_1$–$C_4$ alkyl), wherein said alkyl, alkenyl, cycloalkyl, cycloalkenyl, phenyl, 1-napthyl, 2-napthyl, or phenyl ($C_1$–$C_4$ alkyl) groups are optionally substituted with a substituent selected from the group consisting of: $C_3$–$C_8$ cycloalkyl, $C_5$–$C_7$ cycloalkenyl, $C_1$–$C_4$ alkyl, $C_2$–$C_4$ alkenyl, hydroxy, halo, hydroxyl, nitro, trifluoromethyl, $C_1$–$C_6$ straight or branched chain alkyl or alkenyl, $C_1$–$C_4$ alkoxy, $C_2$–$C_4$ alkenyloxy, phenoxy, benzyloxy, amino, and $Ar_1$, where $Ar_1$ is selected from the group consisting of 1-napthyl, 2-napthyl, and phenyl, and where $Ar_1$ has one to three substituents which are independently selected from the group consisting of hydrogen, halo, hydroxyl, nitro, trifluoromethyl, $C_1$–$C_6$ straight or branched chain alkyl, $C_2$–$C_6$ straight or branched chain alkenyl, $C_1$–$C_4$ alkoxy or $C_2$–$C_4$ alkenyloxy, phenoxy, benzyloxy, and amino; or a pharmaceutically acceptable salt, hydrate or mixture thereof;

ii) an effective amount of an additional therapeutic agent selected from the group consisting of therapeutic hormones, chemotherapeutic agents, monoclonal antibodies, anti-angiogenisis agents, radiolabelled compounds, and a mixture thereof; and (iii) a suitable pharmaceutical carrier.

2. A method of inhibiting prostatic adenocarcinoma tumor cell growth which comprises: administering to said tumor cell or cells an effective amount of a composition of claim 1.

3. A method of inhibiting NAALADase enzyme activity which comprises: administering to said NAALADase enzyme an effective amount of a composition of claim 1.

4. A pharmaceutical composition comprising:

i) a compound selected from the group consisting of:
2-[[methylhydroxyphosphinyl]methyl]pentanedioic acid;
2-[[ethylhydroxyphosphinyl]methyl]pentanedioic acid;
2-[[propylhydroxyphosphinyl]methyl]pentanedioic acid;
2-[[butylhydroxyphosphinyl]]methyl]pentanedioic acid;
2-[[cylohexylhydroxyphosphinyl]methyl]pentanedioic acid;
2-[[phenylhydroxyphosphinyl]]methyl]pentanedioic acid;
2-[[(phenylmethyl) hydroxyphosphinyl]methyl] pentanedioic acid;
2-[[((2-phenylethyl)methyl)hydroxyphosphinyl] methyl]pentanedioic acid;
2-[[((3-phenylpropyl)methyl)hydroxyphosphinyl] methyl]pentanedioic acid;
2-[[((3-phenylbutyl)methyl)hydroxyphosphinyl] methyl]pentanedioic acid;
2-[[((2-phenylbutyl)methyl)hydroxyphosphinyl] methyl]pentanedioic acid;
2-[[(4-phenylbutyl) hydroxyphosphinyl]methyl] pentanedioic acid;
2-[[(aminomethyl) hydroxyphosphinyl]]methyl] pentanedioic acid;
and a pharmaceutically acceptably salt, hydrate or mixture thereof;

ii) an effective amount of an additional therapeutic agent selected from the group consisting of therapeutic hormones, chemotherapeutic agents, monoclonal antibodies, anti-angiogenesis agents, radiolabelled compounds, and a mixture thereof; and (iii) a suitable pharmaceutical carrier.

5. A method of inhibiting prostatic adenocarcinoma tumor cell growth which comprises: administering to said tumor cell or cells an effective amount of a composition of claim 4.

6. A method of inhibiting NAALADase enzyme activity which comprises: administering to said NAALADase enzyme an effective amount of a composition of claim 4.

7. A pharmaceutical composition comprising:

i) a compound selected from the group consisting of:
2-[[methylhydroxyphosphinyl]methylpentanedioic acid;
2-[[ethylhydroxyphosphinyl]methyl]pentanedioic acid;
2-[[propylhydroxyphosphinyl]methyl]pentanedioic acid;
2-[[phenylhydroxyphosphinyl]methyl]pentanedioic acid;
2-[[phenylmethylhydroxyphosphinyl]methyl] pentanedioic acid;
and a pharmaceutically acceptable salt, hydrate or a mixture thereof;

ii) an effective amount of an additional therapeutic agent selected from the group consisting of therapeutic hormones, chemotherapeutic agents, monoclonal antibodies, anti-angiogenesis agents, radiolabelled compounds, and a mixture thereof; and (iii) a suitable pharmaceutical carrier.

8. A method of inhibiting prostatic adenocarcinoma tumor cell growth which comprises: administering to said tumor cell or cells an effective amount of a composition of claim 7.

9. A method of inhibiting NAALADase enzyme activity which comprises: administering to said NAALADase enzyme an effective amount of a composition of claim 7.

* * * * *

UNITED STATES PATENT AND TRADEMARK OFFICE
CERTIFICATE OF CORRECTION

PATENT NO. : 5,880,112
DATED : March 9, 1999
INVENTOR(S) : Paul F. JACKSON et al.

It is certified that error appears in the above-identified patent and that said Letters Patent is hereby corrected as shown below:

Column 25, line 31, after "phenyl, 1-" and before ",",
 please replace "napthyl" with --naphthyl--.

Column 25, line 32, after "2-" and before ", and phenyl",
 please replace "napthyl" with --naphthyl--.

Column 25, line 34, after "1-" and before ", 2-",
 please replace "napthyl" with --naphthyl--.

Column 25, line 34, after "2-" and before ", or phenyl",
 please replace "napthyl" with --naphthyl--.

Column 25, line 42, after "of 1-" and before ", 2-",
 please replace "napthyl" with --naphthyl--.

Column 25, line 42, after ", 2-" and before ",",
 please replace "napthyl" with --naphthyl--.

Signed and Sealed this

Twenty-ninth Day of June, 1999

Attest:

Q. TODD DICKINSON

*Attesting Officer*   *Acting Commissioner of Patents and Trademarks*